(12) United States Patent
Ball et al.

(10) Patent No.: US 11,654,032 B2
(45) Date of Patent: *May 23, 2023

(54) MODULAR INTERBODY SPACER (71) Applicant: Hieu Ball, Walnut Creek, CA (US)

(72) Inventors: Hieu T. Ball, Walnut Creek, CA (US); Lance M. Middleton, Soddy Daisy, TN (US)

(73) Assignee: Hieu T. Ball, Walnut Creek, CA (US)

( * ) Notice: Subject to any disclaimer, the term of this patent is extended or adjusted under 35 U.S.C. 154(b) by 774 days.

This patent is subject to a terminal disclaimer.

(21) Appl. No.: 16/691,733

(22) Filed: Nov. 22, 2019

(65) Prior Publication Data

US 2020/0100906 A1    Apr. 2, 2020

Related U.S. Application Data

(63) Continuation of application No. 16/035,485, filed on Jul. 13, 2018, now Pat. No. 10,517,740, which is a continuation of application No. 15/612,817, filed on Jun. 2, 2017, now Pat. No. 10,034,766, which is a continuation of application No. 15/050,160, filed on Feb. 22, 2016, now Pat. No. 9,693,875, which is a continuation of application No. 13/967,115, filed on Aug. 14, 2013, now Pat. No. 9,295,561.

(60) Provisional application No. 61/682,917, filed on Aug. 14, 2012.

(51) Int. Cl.
*A61F 2/44* (2006.01)
*A61B 17/80* (2006.01)
*A61B 17/86* (2006.01)
*A61F 2/30* (2006.01)

(52) U.S. Cl.
CPC ........ *A61F 2/4455* (2013.01); *A61B 17/8047* (2013.01); *A61F 2/442* (2013.01); *A61B 17/8033* (2013.01); *A61B 17/86* (2013.01); *A61F 2002/302* (2013.01); *A61F 2002/3082* (2013.01); *A61F 2002/3093* (2013.01); *A61F 2002/30112* (2013.01); *A61F 2002/30387* (2013.01); *A61F 2002/30622* (2013.01); *A61F 2002/30677* (2013.01); *A61F 2002/30784* (2013.01); *A61F 2002/30787* (2013.01)

(58) Field of Classification Search
CPC .................. A61F 2/4455; A61F 2/442; A61F 2002/30112; A61F 2002/302; A61F 2002/30387; A61F 2002/30622; A61F 2002/30677; A61F 2002/30784; A61F 2002/30787; A61F 2002/3082; A61F 2002/3093; A61B 17/8047; A61B 17/8033; A61B 17/86
USPC ..................................................... 623/17.16
See application file for complete search history.

(56) References Cited

U.S. PATENT DOCUMENTS

486,477 A    11/1892    Kinsman
5,609,635 A    3/1997    Michelson
(Continued)

*Primary Examiner* — Eduardo C Robert
*Assistant Examiner* — David C Comstock
(74) *Attorney, Agent, or Firm* — Ulmer & Berne LLP; Vance V. VanDrake, II (57) ABSTRACT

An intervertebral spinal spacer system includes a first portion of a modular spacer, the first portion having an upper surface, a lower surface, and an outer surface, and a second portion of the modular spacer, the second portion having an upper surface a lower surface, and an outer surface. The first portion is selectively engageable with the second portion. The first portion and the second portion each define an internal cavity extending from the respective upper surface to the respective lower surface.

19 Claims, 10 Drawing Sheets (56) References Cited

U.S. PATENT DOCUMENTS

| | | | |
|---|---|---|---|
| 5,861,041 A | 1/1999 | Tienboon | |
| 6,113,638 A | 9/2000 | Williams et al. | |
| 6,315,797 B1 | 11/2001 | Middleton | |
| 6,454,806 B1 * | 9/2002 | Cohen | A61F 2/4465 623/17.15 |
| 6,733,535 B2 | 5/2004 | Michelson | |
| 9,295,561 B2 | 3/2016 | Ball et al. | |
| 10,517,740 B2 * | 12/2019 | Ball | A61F 2/442 |
| 2004/0010313 A1 | 1/2004 | Aston et al. | |
| 2004/0102845 A1 | 5/2004 | Reynolds | |
| 2008/0177389 A1 | 7/2008 | Parrish | |
| 2009/0030520 A1 * | 1/2009 | Biedermann | A61F 2/4455 606/301 |
| 2009/0036987 A1 | 2/2009 | Oh et al. | |
| 2009/0254182 A1 | 10/2009 | Kovarik et al. | |
| 2010/0042218 A1 | 2/2010 | Nebosky et al. | |
| 2010/0262245 A1 * | 10/2010 | Alfaro | A61F 2/4465 606/94 |
| 2011/0230971 A1 | 9/2011 | Donner et al. | |
| 2012/0078315 A1 * | 3/2012 | Sweeney | A61F 2/442 606/86 A |
| 2012/0265303 A1 * | 10/2012 | Refai | A61F 2/4465 623/17.11 |
| 2015/0164653 A1 * | 6/2015 | Kueenzi | A61F 2/4455 623/17.16 |

* cited by examiner

MODULAR INTERBODY SPACER

REFERENCE TO RELATED APPLICATION

The present application is a continuation of U.S. non-provisional patent application Ser. No. 16/035,485, filed Jul. 13, 2018, which is a continuation of U.S. non-provisional patent application Ser. No. 15/612,817, filed on Jun. 2, 2017, now U.S. Pat. No. 10,034,766, which is a continuation of U.S. non-provisional patent application Ser. No. 15/050,160, filed on Feb. 22, 2016, now U.S. Pat. No. 9,693,875, which is a continuation of U.S. non-provisional patent application Ser. No. 13/967,115, filed Aug. 14, 2013, now U.S. Pat. No. 9,295,561, which claims the priority benefit of U.S. provisional patent application Ser. No. 61/682,917, filed Aug. 14, 2012, and hereby incorporates the same applications herein by reference in their entirety.

TECHNICAL FIELD

An interbody spacer is provided and, more particularly, an interbody spacer having fluid passages to facilitate the flow of bone marrow and blood elements rich in mesenchymal or undifferentiated hematologic cells and growth factors.

BACKGROUND

Human intervertebral discs generally serve two functions, they cushion and allow movement between pairs of vertebrae. Cushioning is performed by a gel-like material, which forms the inner part of the discs. A fibrous outer layer surrounds the inner gel-like material. Discs are subjected to a great many strains and stresses and are known to deteriorate with age, injury, or disease. When discs are damaged or diseased, the mobility of the subject is often impaired and great pain may result from movement. Damaged discs may also place pressure on the spinal column, causing pain.

SUMMARY

Embodiments of an interbody spacer described herein can include an intervertebral spinal spacer that can include a substantially annular body having an upper surface, a lower surface, an outer surface, and an inner surface, where the inner surface of the substantially annular body can define an internal cavity. The spinal spacer can include a plurality of outer apertures, where the plurality of outer apertures can be defined by the upper surface or the lower surface of the substantially annular body. The spinal spacer can include a plurality of inner apertures, where the plurality of inner apertures can be defined by the inner surface of the substantially annular body. The spinal spacer can include a plurality of fluid passages that can be defined by the substantially annular body and can connect each respective outer aperture to a corresponding inner aperture, where each fluid passage can be configured such that fluid can communicate from the plurality of outer passages, through the plurality of fluid passages, and into the internal cavity of the substantially annular body.

Embodiments of an interbody spacer can include a zero profile intervertebral spinal spacer that can include a substantially annular body that can have an upper surface, a lower surface, an outer surface, and an inner surface, where the inner surface of the substantially annular body can define an internal cavity, where the substantially annular body can include a first modular portion and a second modular portion. The spinal spacer can include a plurality of outer apertures, where the plurality of outer apertures can be defined by the upper surface and the lower surface of the substantially annular body. The spinal spacer can include a plurality of inner apertures, where the plurality of inner apertures can be defined by the inner surface of the substantially annular body. The spinal spacer can include a plurality of substantially L-shaped fluid passages that can be defined by the substantially annular body and can connect the plurality of outer apertures to the plurality of inner apertures, where the plurality of fluid passages can be configured such that a fluid can communicate from the plurality of outer passages, through the plurality of fluid passages, and into the internal cavity of the substantially annular body. The spinal spacer can include at least one bone screw that can be configured to attach the substantially annular body to an anatomical structure. The spinal spacer can include an instrument conduit that can be defined by the substantially annular body, where the instrument conduit can extend from the inner surface to the outer surface of the substantially annular body, where the instrument conduit can be configured to accept a suction device such that a partial vacuum can be present within the internal cavity of the substantially annular body to actively draw the fluid through the plurality of fluid passages.

Embodiments of an interbody spacer can include an intervertebral spinal spacer that can include a substantially annular body having an upper surface, a lower surface, an outer surface, and an inner surface, where the inner surface of the substantially annular body can define an internal cavity. The spinal spacer can include means for drawing fluid into the internal cavity of the substantially annular body and means for attaching the substantially annular body to an anatomical structure.

Embodiments can include an interbody spacer that can include an annular body that can define an internal cavity and a fluid passage, where the annular body can include a first end surface configured for fixation to bone and a second end surface configured for fixation to bone, where the internal cavity can be substantially oriented about a vertical axis. The fluid passage can include a first aperture associated with the first end surface and a second aperture associated with the internal cavity.

Embodiments of an interbody spacer can include an annular body that can include an internal cavity and a fluid passage, where the annular body can include a first end surface configured for fixation to bone and a second end surface configured for fixation to bone, where the fluid passage can have a first boundary portion associated with the first end surface and can have a second boundary portion within the internal cavity.

An interbody spacer can include an annular body having an internal cavity, where the annular body can extend from a first end surface adapted for fixation to bone to a second end surface configured for fixation to bone, where the annular body can have a fluid passage that can have a first boundary portion associated with the first end surface and a second boundary portion that can be associated with the internal cavity.

Embodiments can include an interbody spacer that can include an annular body that can define an internal cavity and a fluid passage, where the annular body can include a first end surface configured for fixation to bone and a second end surface configured for fixation to bone, where the fluid passage can include a first aperture associated with the first end surface and a second aperture associated with the internal cavity.

BRIEF DESCRIPTION OF THE DRAWINGS

It is believed that certain embodiments will be better understood from the following description taken in conjunction with the accompanying drawings in which.

DETAILED DESCRIPTION

Embodiments herein describe an interbody spacer and methods for fixation of adjacent bone segments. Versions of the interbody spacer can be configured with fluid passages for the delivery of beneficial substances external to the interbody spacer including endogenous and exogenous hematopoietic and/or growth factors to, for example, an internal cavity that can be filled with bone graft materials, autogenous bone, allograft bone, or bone graft substitutes (such as collagen based products, demineralized bone graft products, and organic or inorganic mixtures such as tricalcium phosphate or hyaluronic acid).

Anterior and anterolateral approaches to the lumbar spine can allow for superior structural support and improved ability to restore lumbar sagittal plane balance. Approximately, eighty percent of the axial load of the spine is located in the anterior column, or along the axis of the vertebral bodies. The most robust interbody implant can be one that has the largest footprint on the vertebrae or across the joint spaces. Anterior and lateral based spinal fusion implants can allow for more complete discectomy than posterior lumbar interbody fusion (PLIF) approaches, and can allow for larger footprint interbody structural devices (e.g., fusion cages) with larger cavities for bone graft or bone graft substitutes. The larger footprint can provide greater surface area for boney fusion to occur, can offer greater structural stability, and can minimize the risk of subsidence of the implant into the vertebral endplates.

Fixation of adjacent bone segments can be used to treat disorders of the musculoskeletal system caused by disease or trauma. In particular, bone can be "fused" together through the growth, repair, or replacement of bone. Example disorders include, long bone fracture, sacroiliac joint disease, and spinal disorders, such as, degenerative disc disease, spondylolisthesis, and scoliosis. It is contemplated that versions of spacers disclosed herein may be used with any suitable anatomical structure including between two joints, vertebrae, or boney surfaces such that, for example, long bone non-unions and sacroiliac joint disease. Fenestrations are designed to facilitate the passive, positive-pressure, and/or vacuum-assisted delivery of autogenous blood, mesenchymal cells or those of a non-differentiated pluripotential lineage (whether autogenous, allogenic, or recombinantly derived), stem cell delivery, or delivery of growth factors.

Arranging fluid passages to transfer beneficial blood and cellular elements from the bony interfaces of bone segments into a central cavity within the interbody spacer can facilitate fusion. In one version, the central cavity of the interbody spacer can be filled with bone graft material. The transferred blood and cellular elements can be beneficial to bone growth and eventual fusion of bony segments. Such beneficial substances can include osteoprogenitor cells, known to be beneficial to bone growth. As an example, an interbody spacer can be used for spinal fusion, a treatment where adjacent vertebras are fused together.

More specifically, the fluid passages of the interbody spacer, which can be in direct interface with bone tissue, can include channels, conduits, fenestrations, hollow or cutting keels, or the like, can allow for the passive flow of autogenous bone marrow, blood, cells or growth factors, and can act to transport, for example, mesenchymal stem cells, osteoprogenitor cells, or undifferentiated pluripotential cells into the cavity of an interbody spacer where they can integrate with other bone graft materials. These fluid passages in the interbody spacer can also be used to actively draw blood and cellular elements via vacuum or suction when, for example, a syringe or other instrument is attached to the interbody spacer.

Figure 1A:
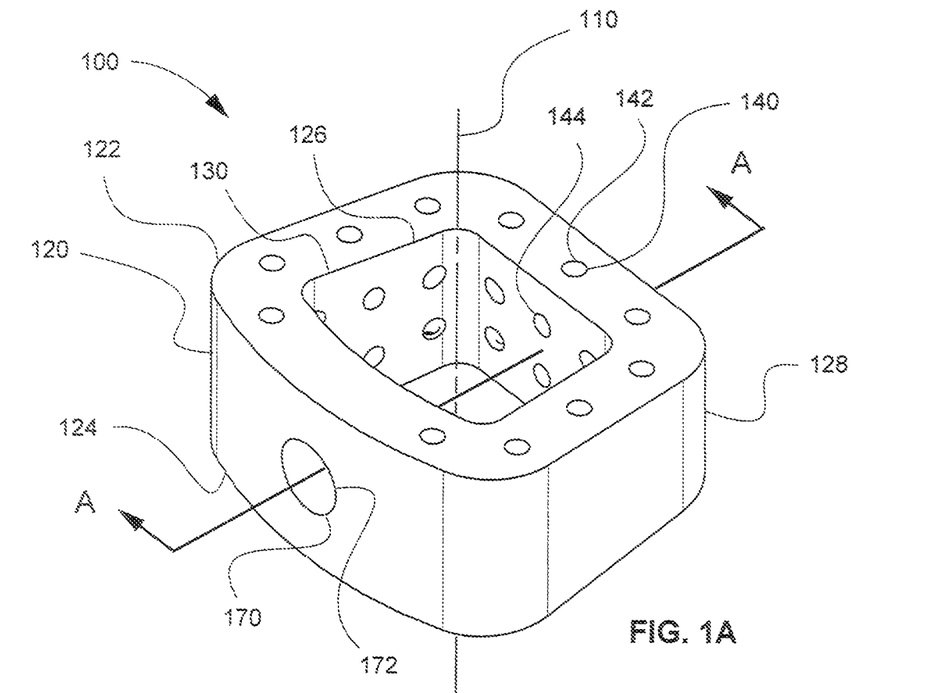
FIG. 1A is a top perspective view depicting an interbody spacer in accordance with one embodiment.
Figure 1B:
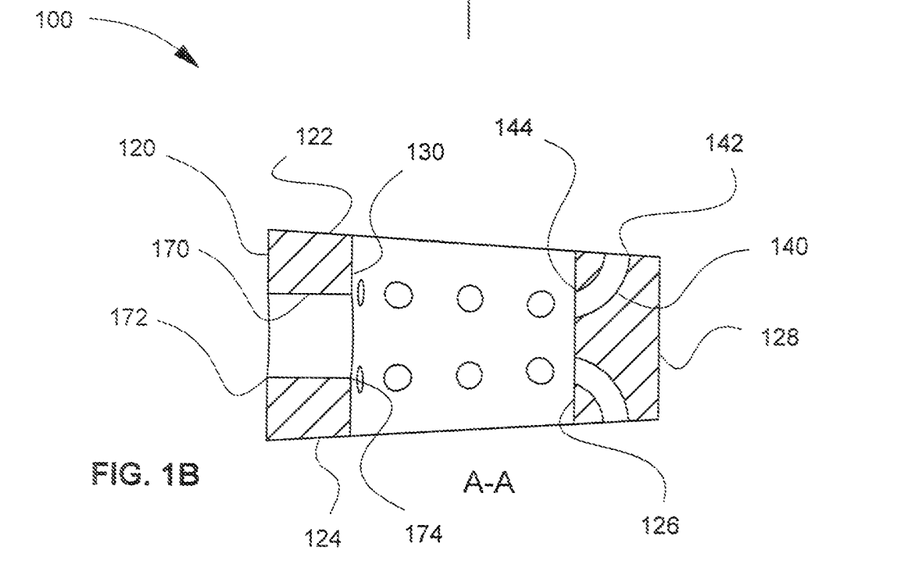
FIG. 1B is a right side cross-sectional view of the interbody spacer of FIG. 1A taken along A-A.

FIG. 1A shows a top perspective view of one version of an interbody spacer 100. FIG. 1B is a cross-sectional view of the interbody spacer of FIG. 1A taken along A-A. Interbody spacer 100 can include a body 120 having an annular shape with respect to a longitudinal axis 110. Body 120 can include a first end surface 122, second end surface 124, inner surface 126, and outer surface 128. First end surface 122 and second end surface 124 can be configured for mechanical or chemical fixation to bone, such as a vertebra. The annular shape of body 120 can establish an internal cavity 130 that can be at least partially defined by inner surface 126. A fluid passage 140 can include a first aperture 142 associated with first end surface 122 and a second aperture 144 associated with inner surface 126 and internal cavity 130.

It will be appreciated that the interbody spacer 100 can include a vertical axis, as illustrated in FIG. 1A, where the internal cavity 130 can be substantially oriented about the vertical axis such that the internal cavity 130 is substantially open at the first end surface 122 and the second end surface 124. Such a configuration may be an improvement over existing fusion cages or fusion baskets, which are generally annular devices having a central cavity oriented about an axis that is perpendicular to the vertical axis shown in FIG. 1A. Fusion cages are generally annular tubes that have a relatively small surface area for bone attachment and this surface area is also generally curved or arcuate. Embodiments of spacers described herein may improve bone attachment by providing a substantially flat or planar surface and a greater surface area relative to existing fusion cages for bone fixation. Orienting the body 120 of the spacer 100 vertically such that the spacer 100 is substantially parallel to vertebrae may also improve stability. It will be appreciated that spacers in accordance with embodiments described herein can be implanted posteriorly.

In one version, interbody spacer 100 can be suitably sized for spinal fusion. Interbody spacer 100 can be positioned in the intervertebral disc space between adjacent vertebral bodies (not shown). Interbody spacer 100 can further be configured for the cervical spine and implanted using an anterior surgical approach, as an example. Annular body 120 can maintain the desired spacing between the vertebral bodies and can support physiologic loading. Internal cavity 130 can be filled with bone graft or other materials suitable to promote bony fusion. Endplates of adjacent vertebral bodies can be prepared for the interbody spacer 100, which can produce advantageous "bleeding bone", a condition that can be advantageous to stimulate bone growth and promote spinal fusion. In one version, cavity 130 can be an open structure, where materials within the cavity, such as bone graft, can be in contact with the bleeding bone. Annular body 120 can include one or a plurality of fluid passages 140. As better illustrated in FIG. 1B, fluid passages 140 are arcuate, but can be any suitable shape and can define straight holes or apertures of any suitable configuration.

First end surface 122 and second end surface 124 can be placed in contact with the vertebral endplates such that blood constituents and bone marrow constituents can be delivered into the first aperture 142, communicate through the fluid passages 140, and flow out of second aperture 144 into the internal cavity 130. The first aperture 142 can be any hole, space, fenestration, or passage that can be located on a surface that interfaces directly or substantially directly with bone. The second aperture 144 can be any hole, space, fenestration, or passage that can interface directly or substantially directly with the internal cavity or the inner surface of the annular body. For example, the first aperture 142 can be positioned adjacent a vertebral endplate and can be configured to receive a fluid, where the fluid can be communicated via the second aperture 144 into the internal cavity of the annular body. In an example embodiment, the first aperture 142 is substantially perpendicular to the second aperture 144. The fluid passages can have any suitable shape, such as an L-shape, to facilitate fluid communication from a region adjacent a bone into the internal cavity of an annular body. The fluid passages can be non-vertical, non-linear, curved, arcuate, of uniform diameter, of varying diameter, or can otherwise be suitably shaped. It will be appreciated that any suitable number of fluid passages, including fluid passages having different shapes, sizes, or purposes, is contemplated. Beneficial constituents within blood and bone marrow can include a variety of growth factors and cells, such as osteoprogenitor cells. In combination with bone graft, bone graft substitute materials, or other materials within internal cavity 130, the blood and cellular elements delivered through fluid passages 140 can promote bone growth and eventual bony fusion.

Fluid passages 140 can also be used to actively draw blood and cellular elements into the internal cavity 130 by applying a negative pressure. Referring again to FIGS. 1A and 1B, radial passage 170 can be a conduit (e.g., an instrument conduit) having outer aperture 172 in association with outer surface 128 and inner aperture 174 in association with inner surface 126. Radial passage 170 can be configured for the selective attachment of a surgical instrument (not shown) that can be used to insert and position interbody spacer 100 between bone segments, including vertebral bodies. With respect to anatomical positioning, radial passage 170 can be associated with the anterior, posterior, or lateral aspect of the device relative to the patient's anatomy, as examples. Radial passage 170 can be configured for use with a suction device, such as a syringe, to create at least a partial vacuum within internal cavity 130 such that blood and cellular elements can be drawn directly into internal cavity 130 or through fluid passages 140. Radial passage 170 can be used to transfer substances into the internal cavity 130 via a syringe or one or a plurality of other instruments suitable for dispensing materials to promote bone growth or for any other suitable purpose.

Figure 2A:
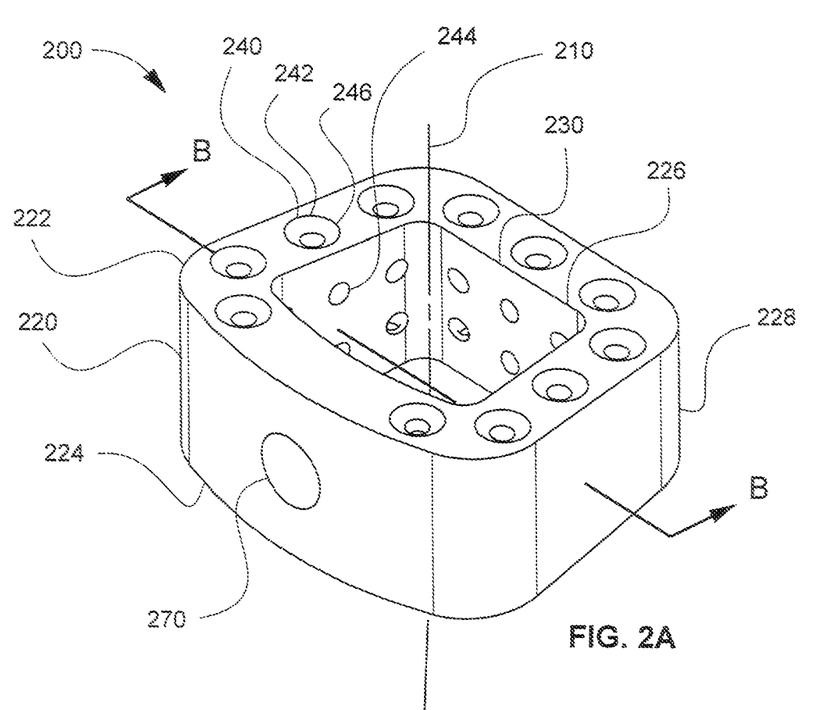
FIG. 2A is a top perspective view depicting an interbody spacer in accordance with another embodiment.
Figure 2B:
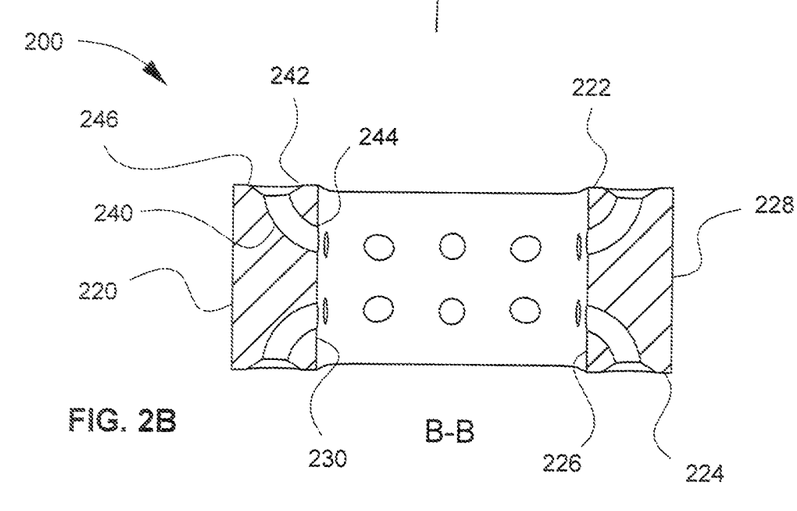
FIG. 2B is side cross-sectional view of the interbody spacer of FIG. 2A taken along B-B.

The one or a plurality of fluid passages can vary in shape of cross-section. As an example, FIG. 2A shows a top perspective view of one version of an interbody spacer 200. FIG. 2B is a cross-section view taken along B-B. Interbody spacer 200 can include a body 220 that can have an annular shape with respect to longitudinal axis 210. Body 220 can include a first end surface 222, a second end surface 224, an inner surface 226, and an outer surface 228. First end surface 222 and second end surface 224 can be configured for fixation to bone. The annular shape of body 220 can establish an internal cavity 230 that can be partially defined by inner surface 226. Fluid passage 240 can include a first aperture 242 that can be associated with first end surface 222 and a second aperture 244 that can be associated with inner surface 226. As an example, fluid passage 240 can be associated with a conical portion 246 such that first aperture 242 has a greater diameter relative to second aperture 244. Working like a funnel, first aperture 242 and conical portion 246 of fluid passage 240 can expose more surface area of prepared bone and can increase the potential area for blood and cellular elements to flow into internal cavity 230.

Bony interface surfaces can be configured for fixation to bone and can include features that can mechanically interlock into bone. Specifically, bony interface surfaces can feature protrusions in the form of a keel, spike, or saw-tooth serration, as examples. These protrusions or surface effects can be singular or patterned, where in a patterned configuration the protrusions can be, for example, raised areas that can form a serration. As an example, interbody spacers or devices for anterior spinal fusion can include a keel that can be aligned with the anterior-posterior direction and can form an attachment surface with a protrusion. As another example, an interbody spacer for spinal fusion can include a saw-tooth design aligned with the medial-lateral direction in the form of serration. A multitude of conical or pointed protrusions (spikes) can be arranged on a bony interface surface. A fluid passage can be integral with or associated with any of these protrusions. In one version, an opening of a fluid passage can be configured near or at the peak of a protrusion, such that the opening of the fluid passage can be nearer or embedded deeper into bone.

Figure 3A:
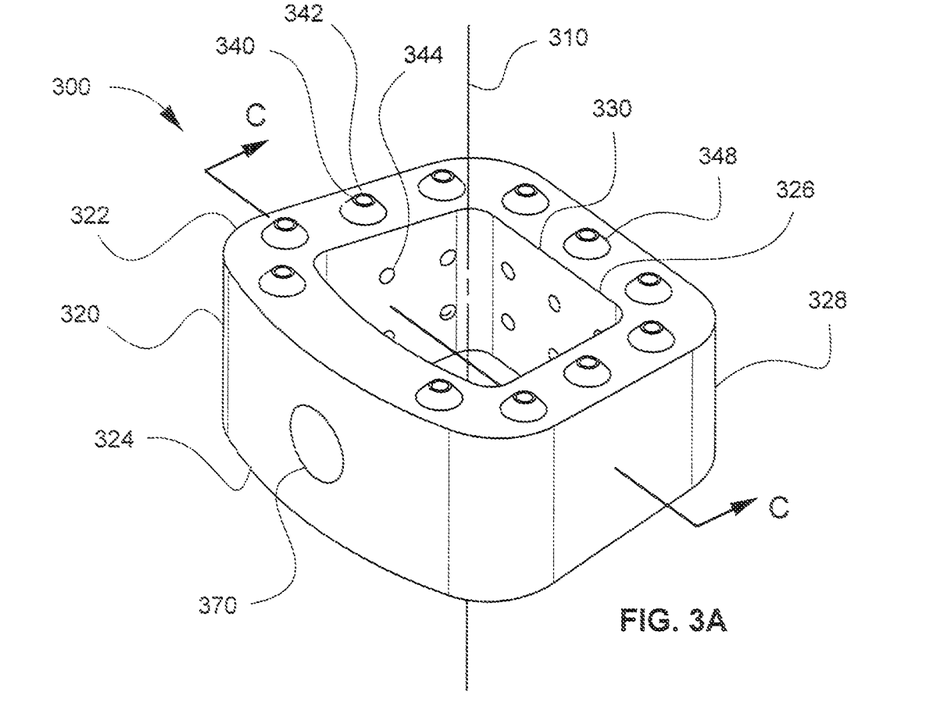
FIG. 3A is a top perspective view depicting an interbody spacer in accordance with another embodiment.
Figure 3B:
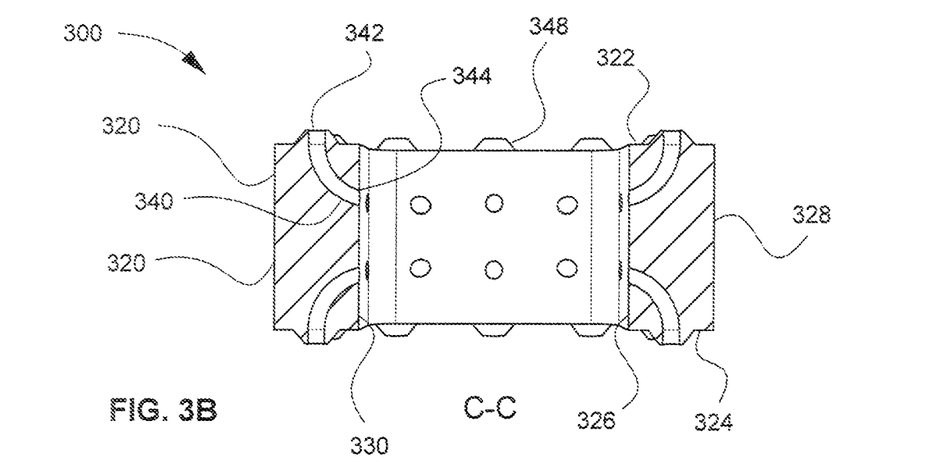
FIG. 3B is side cross-sectional view of the interbody spacer of FIG. 3A taken along C-C.

One version of an interbody spacer 300 is shown in FIG. 3A and FIG. 3B. Interbody spacer 300 can include a body 320 having an annular shape with respect to a longitudinal axis 310. Body 320 can include a first end surface 322, a second end surface 324, an inner surface 326, and an outer surface 328. First end surface 322 and second end surface 324 can be configured for fixation to bone. The annular shape of body 320 can establish an internal cavity 330 that can be partially defined by inner surface 326. First end surface 322 can include a plurality of conical protrusions 348. Fluid passage 340 can include a first aperture 342 that can be associated with first end surface 322, located at the apex of conical protrusion 348. Second aperture 344 can be associated with inner surface 326 and internal cavity 330.

Previously discussed embodiments feature closed fluid passages, but open fluid passages can also be incorporated to transfer blood and cellular elements into an internal cavity. In addition, the internal cavity can have any suitable volume, such as a volume greater than the cavities shown, such that additional bone graft material can be used. The internal cavity can include a relatively large opening at the bone interface, which can facilitate maximum contact with surgically prepared bone, which can include bone scraped or otherwise cut or treated to allow blood and cellular elements to integrate with bone graft material within an interbody spacer. Fluid passages can be configured to increase the volume of a cavity and can increase the contact area for bone graft materials and prepared bone, such as bleeding bone.

Figure 4A:
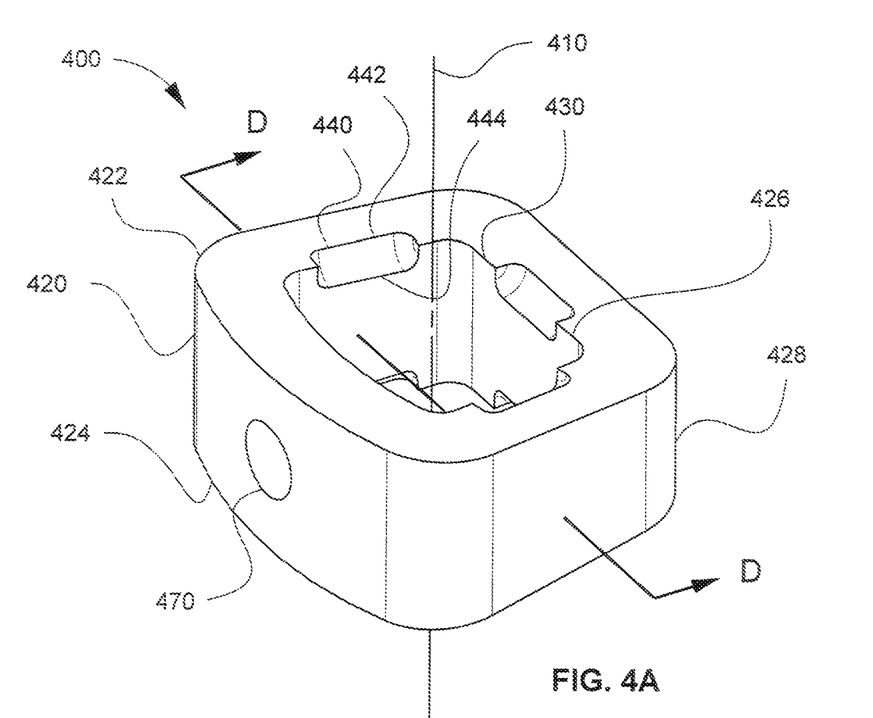
FIG. 4A is a top perspective view depicting an interbody spacer in accordance with another embodiment.
Figure 4B:
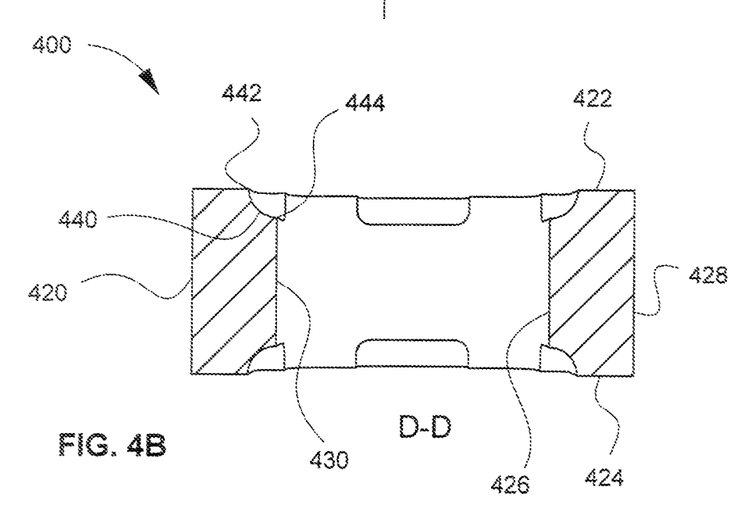
FIG. 4B is side cross-sectional view of the interbody spacer of FIG. 4A taken along D-D.

FIG. 4A shows a top perspective view of one version of an interbody spacer 400. FIG. 4B is a cross-section view taken along D-D. Interbody spacer 400 can include a body 420 that can have an annular shape with respect to a longitudinal axis 410. Body 420 can include a first end surface 422, a second end surface 424, an inner surface 426, and an outer surface 428. First end surface 422 and second end surface 424 can be configured for fixation to bone. Fluid passage 440 can include a first boundary 442 associated with first end surface 422 and a second boundary 444 associated with inner surface 426. The annular shape of body 420 can establish an internal cavity 430 that can be partially defined by inner surface 426 and fluid passages 440. Fluid passage 440 can include one or a plurality of open passages or recessed portions, which can expand internal cavity 430 at the juncture between the first end surface 422 and inner surface 426.

Figure 5A:
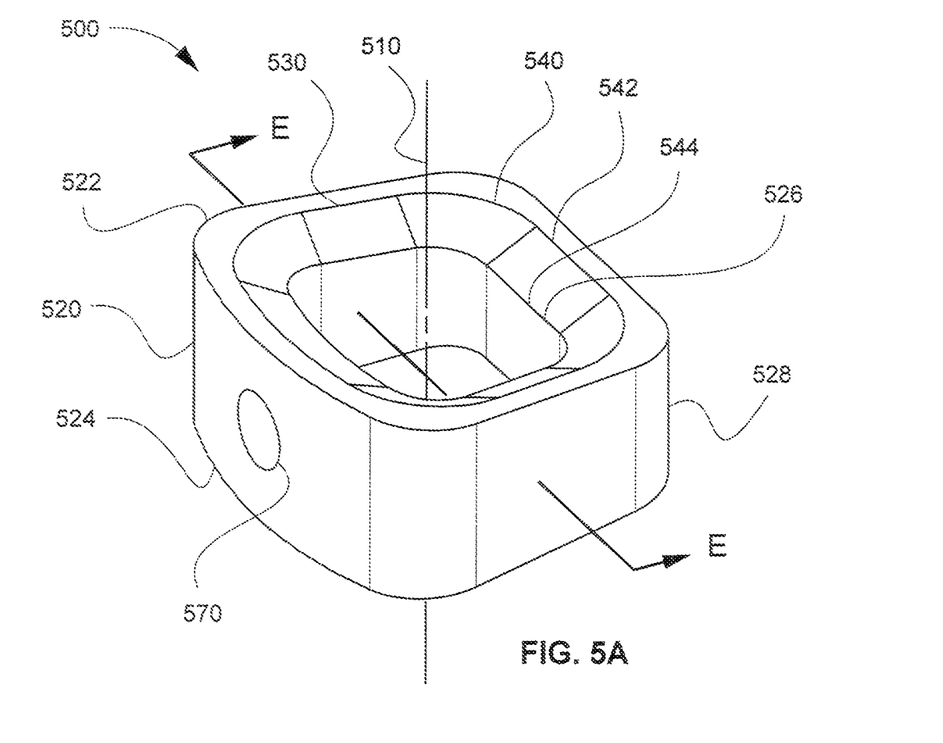
FIG. 5A is a top perspective view depicting an interbody spacer in accordance with another embodiment.
Figure 5B:
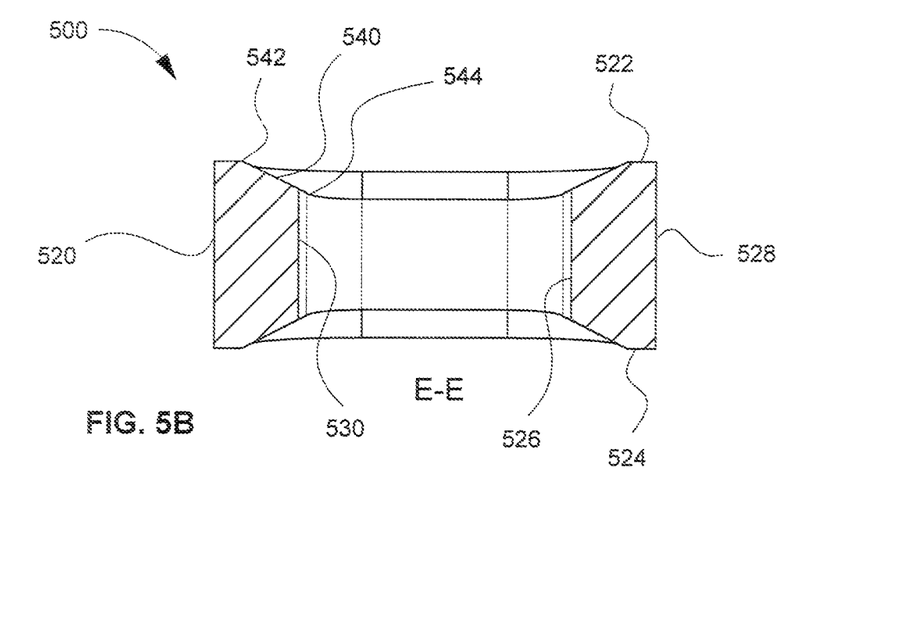
FIG. 5B is side cross-sectional view of the interbody spacer of FIG. 5A taken along E-E.

Interbody spacer 500, shown in FIG. 5A and FIG. 5B, can include a body 520 that can have an annular shape with respect to a longitudinal axis 510. Body 520 can include a first end surface 522, a second surface 524, an inner surface 526, and an outer surface 528. First end surface 522 and second end surface 524 can be configured for fixation to bone. The annular shape of body 520 can establish an internal cavity 530 that can be partially defined by inner surface 526 and fluid passage 540. Fluid passage 540, can be in the form of a chamfer, and can include a first boundary 542 associated with a first end surface 522 and a second boundary 544 at the juncture with inner surface 526. First boundary 542 can be proximate to outer surface 528 and can increase the volume of internal cavity 530 and can enlarge internal cavity 530 at a bony interface. Alternatively, first boundary 542 can be centrally located between inner surface 526 and outer surface 528. Inner surface 526 and fluid passages 540 can result in cavity 530 having a generally hourglass shape, wherein internal cavity 530 can be wider at its ends.

Figure 6A:
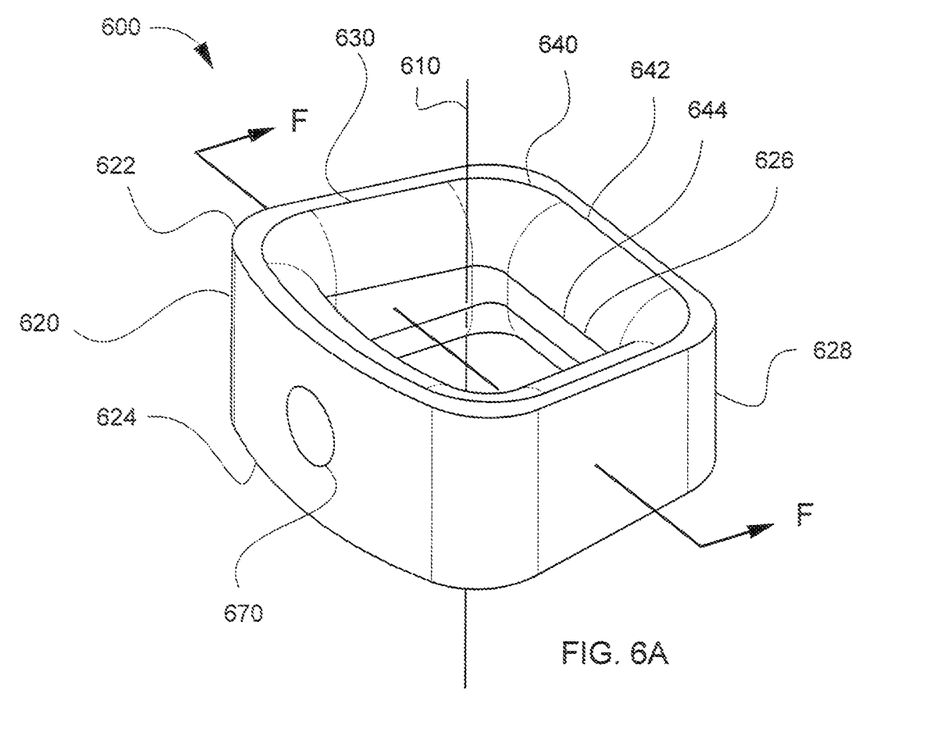
FIG. 6A is a top perspective view depicting an interbody spacer in accordance with another embodiment.
Figure 6B:
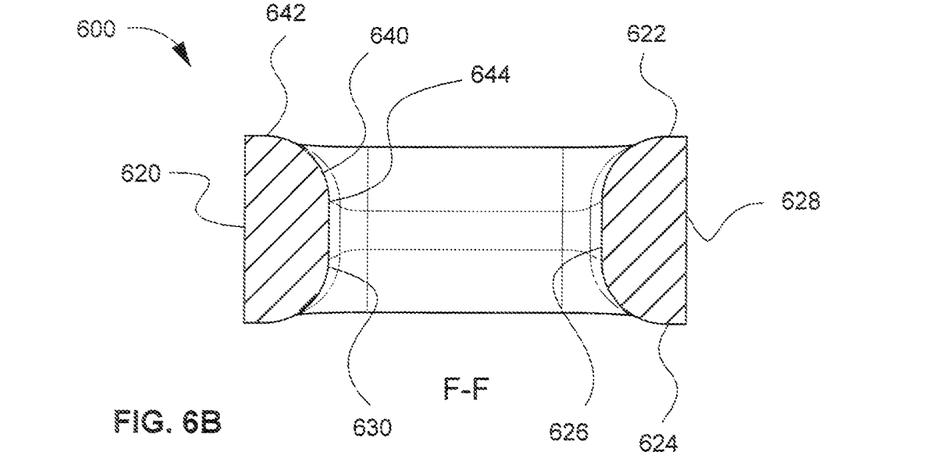
FIG. 6B is side cross-sectional view of the interbody spacer of FIG. 5A taken along F-F.

Interbody spacer 600, shown in FIG. 6A and FIG. 6B, can include a body 620 that can have an annular shape with respect to a longitudinal axis 610. Body 620 can include a first end surface 622, a second end surface 624, an inner surface 626, and an outer surface 628. First end surface 622 and second end surface 624 can be configured for fixation to bone. The annular shape of body 620 can establish an internal cavity 630 that can be partially defined by inner surface 626 and fluid passage 640. Fluid passage 640, which can have a round form, can include a first boundary 642 associated with a first end surface 622 and a second boundary 644 at the juncture with inner surface 626. First boundary 642 can be proximate to outer surface 628 and can increase the volume of internal cavity 630 and can enlarge internal cavity 630 at a bony interface. Alternatively, first boundary 642 can be centrally located between inner surface 626 and outer surface 628. Inner surface 626 and fluid passages 640 can result in internal cavity having a generally hourglass shape, wherein internal cavity 630 can be wider at its ends.

Figure 7:
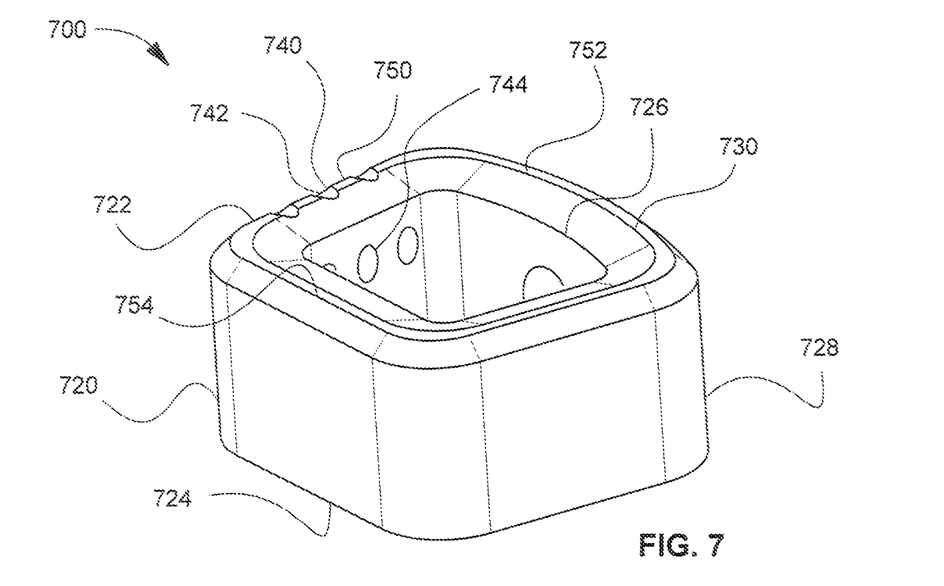
FIG. 7 is a top perspective view depicting an interbody spacer in accordance with another embodiment.

Fluid passages intended for the flow of blood and other fluid constituents can be combined with bony interface surfaces to form a serrated surface that can enhance attachment to bone. This can be accomplished by fluid passages that are open cross-sections, closed cross-sections, or combinations thereof. As an example, interbody spacer 700 of FIG. 7 can include a body 720 that can include an annular shape, a first end surface 722, a second surface 724, an inner surface 726, an outer surface 728, an inner chamfer 752, and an outer chamfer 754. First end surface 722, which can be configured for fixation to bone, can include an internal chamfer 752, an outer chamfer 754, and an exemplary peak 750. The annular shape of body 720 can establish an internal cavity 730 that can be partially defined by inner surface 726 and internal chamfer 752. Fluid passage 740 can include a hole or aperture with a generally circular cross-section. The ends of fluid passage 740 can be defined by first boundary 742 associated with first end surface 722 and second boundary 744 at the juncture with inner surface 726. A plurality of fluid passages 740 intersecting first end surface 722 can define a plurality of peaks 750 and can form a serration that can enhance fixation of the interbody spacer 700 to bone.

Figure 8:
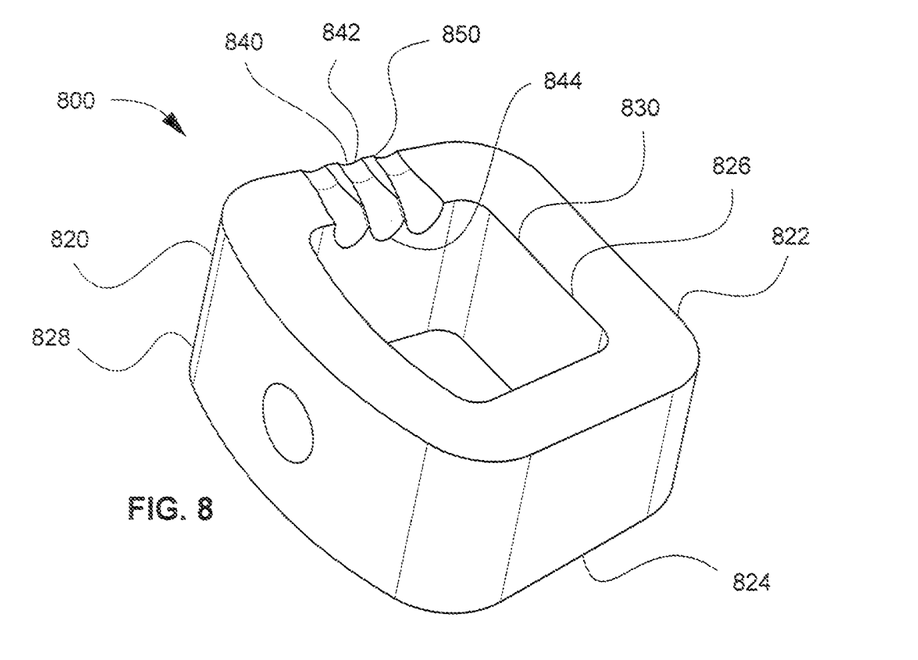
FIG. 8 is a top perspective view depicting an interbody spacer in accordance with another embodiment.

Interbody spacer 800, shown in FIG. 8, can include a body 820 that can have an annular shape. Body 820 can include a first end surface 822, a second end surface 824, an inner surface 826, and an outer surface 828. First end surface 822 and second end surface 824 can be configured for fixation to bone. The annular shape of body 820 can establish an internal cavity 830 that can have a boundary partially defined by inner surface 826. Fluid passages 840 can include a first boundary 842 associated with the juncture of first end surface 822 and outer surface 828. Second boundary 844 can be associated with inner surface 826 and internal cavity 830. Fluid passage 840 can follow an arcuate path directed toward the central region of internal cavity 830. The annular shape of body 820 can establish an internal cavity 830 that can be partially defined by inner surface 826. Fluid passage 840 can be patterned to form peak 850, further defining a serration that can enhance fixation to bone.

A surgeon can have an initial implant strategy and implant system prepared for a patient, but conditions discovered or occurring intraoperatively can result in the desire to have a different implant system. One version of an interbody spacer system can include interchangeable elements to provide for variations in anatomical size or shape and can allow for a more tailored fit with respect to the anterior-posterior plane of the intervertebral space, and the optional use of supplementary fixation elements. Various fixations elements can be useful to achieve desired levels of fixation and stability. Accordingly, an interbody spacer system can be configured as a modular interbody spacer, where the modular interbody spacer can include fixation elements that can maintain implant position (e.g., an interference screw). A modular interbody spacer can include fixation elements that can provide additional stability to targeted bone segments.

The width-to-depth ratio of the lumbar vertebrae can vary between patients. Existing implant systems typically allow for small/medium and large/extra large cages with fixed ratios of lateral and anterior-posterior sizing. Often, either the anterior-posterior depth, or the inability to gain extensile exposure of the anterior vessels can force the surgeon to select a smaller side-to-side dimensioned cage to safely insert it into the intradiscal space. The smaller side-to-side cages can lack the appropriate anterior-posterior depth to optimize fusion surface area.

A modular interbody spacer system and method can include, for example, the following, (1) selecting a first component for insertion into an intervertebral disc space, (2) selecting and using a second component for interconnection with the first component, and (3) selecting a fixation element. The second component can have attributes that can contribute to the size and shape of the interbody spacer system and can include holes or other features that can enable the attachment of fixation elements, such as screws.

Figure 9:
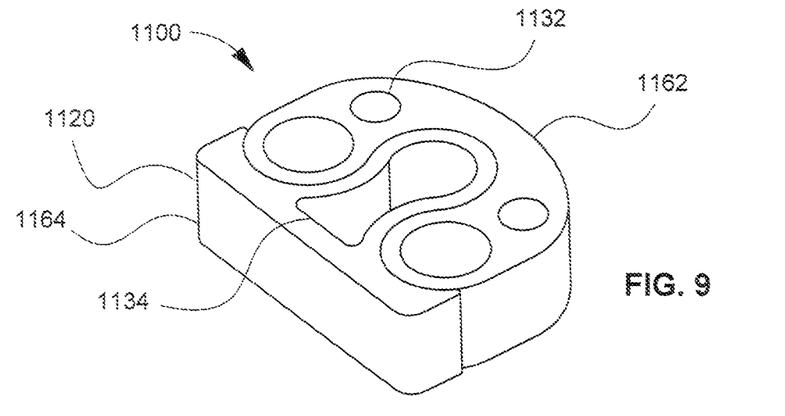
FIG. 9 is a top perspective view depicting a modular interbody spacer in accordance with one embodiment.

FIG. 9 shows one embodiment of a modular interbody spacer 1100 that can be configured for fixation of adjacent bone segments. Modular body 1120 can include a first component 1162 and a second component 1164. First component 1162 can be associated with one of more internal cavities, such as internal cavity 1132 and second component 1164 can include an internal cavity 1134. As described herein, internal cavities can be filled with bone graft or other materials that can promote bone growth and fusion. The bony interfaces of modular body 1120 can be further adapted with spikes, keels, or porous coatings, as examples, that can facilitate attachment to bone. First component 1162 and second component 1164 can be arranged in an interlocking manner. As shown, modular interbody spacer 1100 can be configured without modular, or supplementary fixation elements (e.g., bone screws). Second component 1164 is shown by way of example, where alternative components can be combined with first component 1162 in a modular manner. It will be appreciated that first component 1162, for example, can be used independently of second component 1164, where the second component 1164 can be a selectively usable option. These alternative components may have various shapes and features to facilitate the use of additional fixation components, such as bone screws, adhesives, screws, pins, or the like. It will be appreciated that any suitable number of components, of any size, shape, or function, can be provided or otherwise make up the modular interbody spacer 1100. Although not shown in FIG. 9 first component 1162 can be configured with fluid passages for the flow of blood into internal cavities, as described in certain other embodiments (see for example FIGS. 1A, 2A, 3A, 4A, 5A, 6A, 7 and 8). These fluid passages can be designed to facilitate the passive, positive-pressure, and/or vacuum-assisted delivery of autogenous blood, mesenchymal cells or those of a non-differentiated pluripotential lineage (whether autogenous, allogenic, or recombinantly derived), stem cell delivery, or delivery of growth factors.

Figure 10:
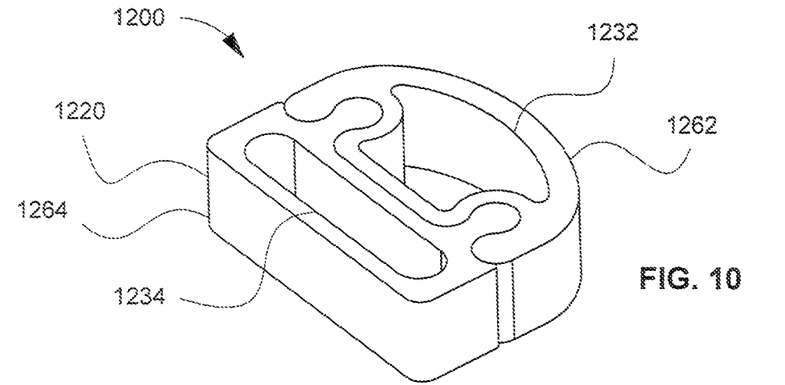
FIG. 10 is a top perspective view depicting a modular interbody spacer in accordance with another embodiment.

FIG. 10 shows one version of an interbody spacer 1200 that can be configured for fixation of adjacent bone segments. Modular body 1220 can include a first component 1262 and a second component 1264. First component 1262 can be associated with internal cavity 1232 and second component 1264 can include an internal cavity 1234. The bony interfaces of modular body 1220 can be configured with spikes, keels, or porous coatings, as examples, that can facilitate attachment to bone. First component 1262 and second component 1264 can be arranged in an interlocking manner or in any other suitable manner such as a snap fit, a tongue and groove, an adhesive, a threaded connection, or the like. As shown, interbody spacer 1200 can be configured without modular, or supplementary fixation elements (e.g., bone screws). Second component 1264 can be combined with first component 1262 in a modular manner. Although not shown in FIG. 10 first component 1262 and second component 1264 can be configured with fluid passages for the flow of blood into internal cavities, as described in certain other embodiments (see for example FIGS. 1A, 2A, 3A, 4A, 5A, 6A, 7 and 8).

Figure 11A:
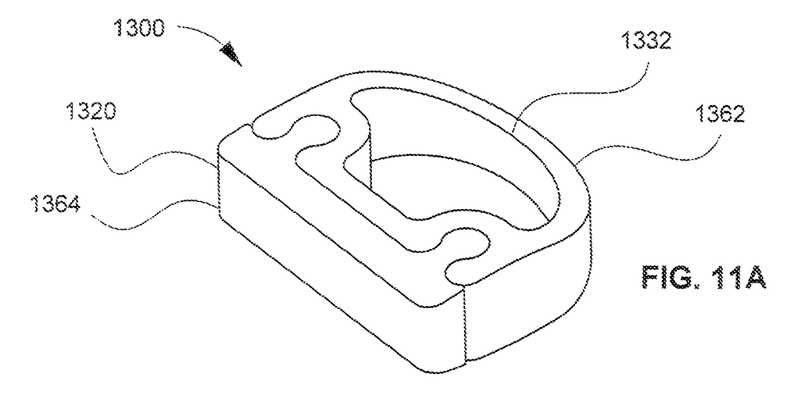
FIG. 11A is a top perspective view depicting a modular interbody spacer in accordance with another embodiment.
Figure 11B:
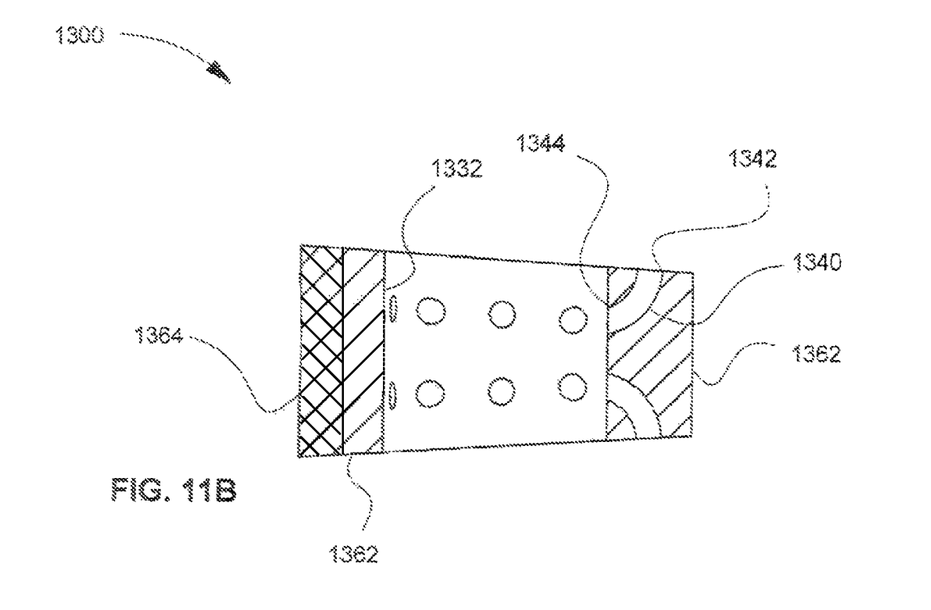
FIG. 11B is a right side cross-sectional view of the modular interbody spacer of FIG. 11A in accordance with another embodiment.

FIG. 11A shows one version of an interbody spacer 1300 that can be configured for fixation of adjacent bone segments. Modular body 1320 can include a first component 1362 and a second component 1364. First component 1362 can be associated with internal cavity 1332. The bony interfaces of modular body 1320 can be further configured with spikes, keels, or porous coatings, as examples, that can facilitate attachment to bone. First component 1362 and second component 1364 can be arranged in an interlocking manner. As shown, interbody spacer 1300 can be configured without modular, or supplementary fixation elements (e.g., bone screws). Second component 1364 can be combined with first component 1362 in a modular manner, or with any other suitable component. These alternative components can have various shapes and features to facilitate the use of additional fixation components, such as, bone screws. At least a portion of second component 1364 can be external to the space between bone fragments to facilitate the placement of bone screws on the outside of bone segments. As shown in FIG. 11B, first component 1362 (base component) can be configured with fluid passages 1340 including a first aperture 1342 and a second aperture 1344 for the flow of blood into internal cavity 1332, as described in certain other embodiments (see for example FIGS. 1A, 2A, 3A, 4A, 5A, 6A, 7 and 8).

Figure 12:
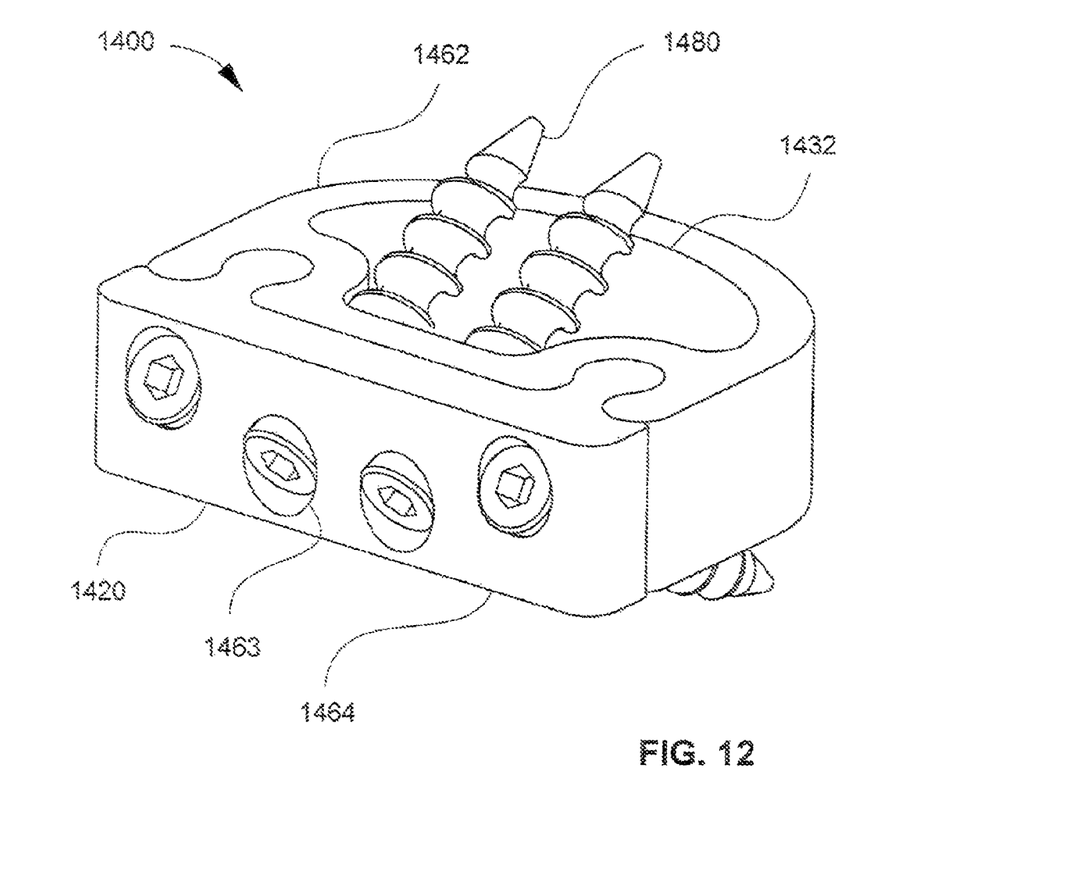
FIG. 12 is a top perspective view depicting a modular interbody spacer in accordance with another embodiment, where the modular spacer is shown with a plurality of bone screws.

Additionally, a second component of an interbody spacer for spinal fusion may allow surgeons to perform the anterior lumbar interbody fusion (ALIF) without the need for additional components, such as, posterior pedicle screws inserted through a second surgical site. FIG. 12 shows one version of an interbody spacer 1400 that can be configured for fixation of adjacent bone segments. Modular body 1420 can include a first component 1462 and a second component 1464. First component 1462 can be associated with internal cavity 1432. The bony interfaces of modular body 1420 can be configured with spikes, keels, or porous coatings, as examples, that can facilitate attachment to bone. First component 1462 and second component 1464 can be arranged in an interlocking manner. As shown, interbody spacer 1400 can be configured with modular, or supplementary fixation elements (e.g., bone screws). Second component 1464 can be configured with holes 1463 (see FIG. 12) that can facilitate the placement of bone screws 1480. Bone screws 1480 can be provided to keep interbody spacer system 1400 in a desired location and can provide additional stability to bone structures. Fixation screws can also be configured to secure first component 1462 to second component 1464. Fixation screws can be 4 total for this option and can be divergent in the cephalad-caudad anatomic plane and/or in the lateral or side-to-side anatomic plane, not convergent or parallel. This configuration may increase rigidity in torsion, flexion, extension and lateral bending, as well as reduce the risk of implant displacement. As an example, bone screws 1480 can be secured into vertebral bodies. Additionally, an anterior metallic plate can be incorporated to allow the metallic screws to lock more securely to the anterior module; in cases where non-metallic screws (ceramic, PEEK, or other material) may be used, the plate can match the material of the screws. A separate modular plate can allow the screws to lock in a metal to metal fashion, or simply lock to the actual cage itself.

The concept of modularity of the ALIF can provide multiple advantages. From an inventory standpoint, cages can be built up to patient-specific sizing in a stacking fashion such that, for example, two or three standard size base units can be used to create a plurality of configurations. If additional depth is needed, for example, a small (2 mm), medium (4 mm), or deep (6 mm) add-on component piece can be coupled with and locked to the base unit cage. A screw hole to provisionally fix to the vertebral bodies can also be designed to help lock the stackable units into place. This can allow for anterior-posterior fusions and can allow for the patient to be turned from supine (anterior fusion) to prone (posterior fusion) without risk of the ALIF displacing during the turning of the patient from supine to prone. Such a system can also allow for surgeons who stage their anterior and posterior procedures across several days to safely allow patients to be ambulatory rather than keeping them on bedrest between the anterior and posterior stages of the fusion.

Figure 13A:
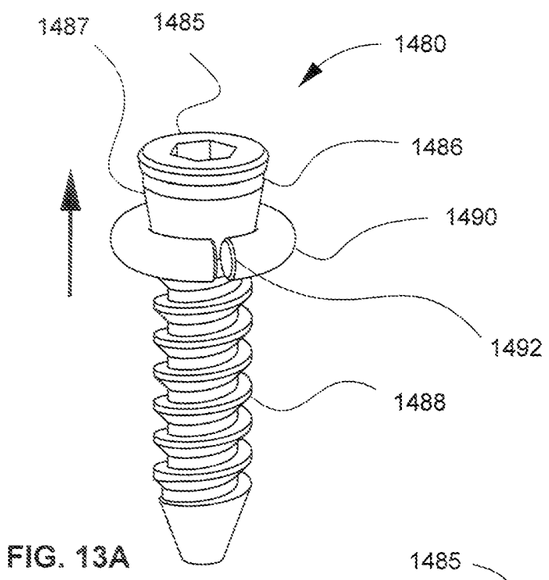
FIG. 13A is a top perspective view depicting a bone screw having a locking ring shown in an unsecured position.
Figure 13B:
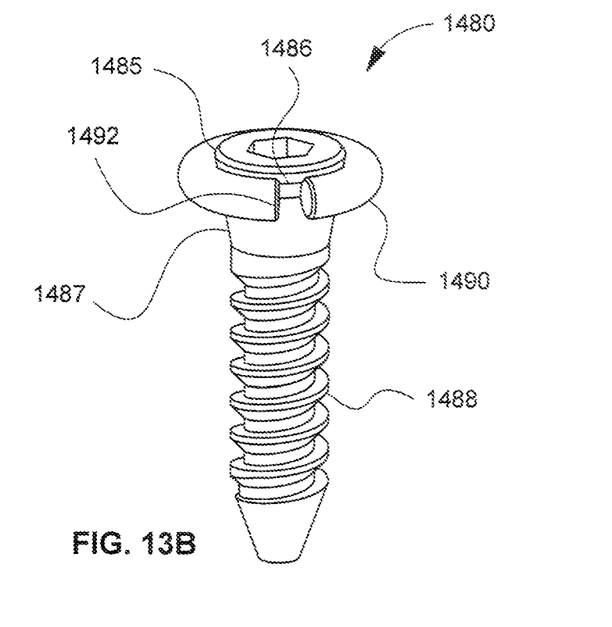
FIG. 13B is a top perspective view of the bone screw of FIG. 13A shown with the locking ring in a secured position.

It can also be advantageous to provide a mechanism for securing a bone screw to an interbody device, such that component parts can be resistant to separation if components loosen during the course of healing. Related to the ability to sterilize and clean components, it can be desirable to have implant components loosely preassembled. FIGS. 13A and 13B show one version of a bone screw 1480 of FIG. 12 that can include screw body 1485 and a locking ring 1490. Screw body 1485 can include a tapered head 1487, a head recess 1486, and a thread 1488. Locking ring 1490 can have an annular shape and can include a split 1492 to allow for expansion. Upon securing bone screw 1480 within hole 1463 of interbody spacer 1400 (see FIG. 12), locking ring 1490 can slide and expands along tapered head 1487, and can be finally secured in an expanded form within head recess 1486, as shown in FIG. 13B. Hole 1463 can be suitably shaped to force locking ring 1490 to slide along tapered head 1487. Hole 1463 can also be suitably shaped or recessed to secure screw 1480, such that the components are resistant to separation. Any configuration or number of screws, locking rings, or the like is contemplated.

All interbody spacers and interbody spacer systems shown may provide "zero profile" or very low profile fixation. As an example of zero profile fixation in spinal fusion, the entirety of the implant can be within the intervertebral disc space to avoid contact with anterior great vessels that run along the front of the spine (inferior vena cava, aorta, iliac veins and arteries). A very low profile configuration can allow part of the implant to perch on the anterior lip of the vertebral body for stability purposes. Materials for the interbody spacer bodies include a variety of structural biomaterials, for example, such as titanium alloy, PEEK, allograft bone, or ceramic, such as silicon nitride, as examples.

In various embodiments disclosed herein, a single component can be replaced by multiple components and multiple components can be replaced by a single component to perform a given function or functions. Except where such substitution would not be operative, such substitution is within the intended scope of the embodiments.

The examples discussed herein are examples only and are provided to assist in the explanation of the apparatuses, devices, systems and methods described herein. None of the features or components shown in the drawings or discussed below should be taken as mandatory for any specific implementation of any of these the apparatuses, devices, systems or methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. An intervertebral spinal spacer comprising:
   (a) a first portion of a modular spacer, the first portion having an upper surface, a lower surface, and an outer surface; and
   (b) a second portion of the modular spacer, the second portion having an upper surface a lower surface, and an outer surface, wherein the first portion is selectively engageable with the second portion, wherein the first portion and the second portion each define an internal cavity extending from the respective upper surface to the respective lower surface; and further comprising:
   at least one fluid passage defined by the first portion or the second portion, the at least one fluid passage being in fluid communication with at least one of the internal cavities, wherein each of the internal cavities has a sidewall extending between an upper opening on the respective upper surface and a lower opening on the respective lower surface of the first portion or the second portion defining the internal cavity, and wherein the at least one fluid passage extends between an inner aperture on the sidewall and an outer aperture on the respective upper surface of the first portion or the second portion.

2. The intervertebral spinal spacer of claim 1, wherein at least one of the first portion or the second portion includes a plurality of outer apertures.

3. The intervertebral spinal spacer of claim 2, wherein the first portion or the second portion includes a plurality of inner apertures, the plurality of inner apertures being defined by an inner surface of an internal cavity defined by the modular spacer.

4. The intervertebral spinal spacer of claim 3, further comprising a plurality of fluid passages defined by the modular spacer and connecting each respective outer aperture to a corresponding inner aperture such that fluid communicates from the plurality of outer apertures, through the plurality of fluid passages, and into the internal cavity defined by the modular spacer.

5. The intervertebral spinal spacer of claim 1, further comprising an instrument conduit, wherein the instrument conduit is a passageway defined by the at least one of the first portion or the second portion.

6. The intervertebral spinal spacer of claim 5, wherein the instrument conduit is sized to receive a suction device.

7. The intervertebral spinal spacer of claim 1, wherein the first portion is operably configured to mate with the second portion such that a customized modular spacer is formed.

8. The intervertebral spinal spacer of claim 1, further comprising at least one fastener to attach the modular spacer to an anatomical structure.

9. The intervertebral spinal spacer of claim 1, wherein the upper surface or the lower surface of the first portion or the second portion includes an interface that facilitates attachment to bone.

10. The intervertebral spinal spacer of claim 1, wherein the modular spacer provides zero profile spinal fusion.

11. The intervertebral spinal spacer of claim 1, where in the first portion includes a first attachment member and the second portion includes a second attachment member such that the first portion and the second portion are interlocked.

12. The intervertebral spinal spacer of claim 1, wherein the first portion of the modular spacer is selectable from a plurality of sizes having different widths such that the first portion is customizable to a patient's anatomy.

13. The intervertebral spinal spacer of claim 12, wherein the second portion of the modular spacer is selectable from a plurality of sizes having different depths such that the second portion is customizable to the patient's anatomy.

14. An intervertebral spinal spacer comprising:
(a) a first portion of a modular spacer, the first portion being selectable from a plurality of spacer elements having different sizes, the first portion having an upper surface, a lower surface, an outer surface, and a first attachment member; and
(b) a second portion of the modular spacer, the second portion being selectable from the plurality of spacer elements having different sizes, the second portion having an upper surface a lower surface, an outer surface, and a second attachment member, wherein the first attachment member is engaged with the second attachment member to interlock the first portion and the second portion, and wherein the first portion and the second portion each define an internal cavity extending from the respective upper surface to the respective lower surface; and further comprising:
at least one fluid passage defined by the first portion or the second portion, the at least one fluid passage being in fluid communication with at least one of the internal cavities, wherein each of the internal cavities has a sidewall extending between an upper opening on the respective upper surface and a lower opening on the respective lower surface of the first portion or the second portion defining the internal cavity, and wherein the at least one fluid passage extends between an inner aperture on the sidewall and an outer aperture on the respective upper surface of the first portion or the second portion.

15. The intervertebral spinal spacer of claim 14, wherein the first portion of the modular spacer is selectable from a plurality of sizes having different widths.

16. The intervertebral spinal spacer of claim 14, wherein the second portion of the modular spacer is selectable from a plurality of sizes having different depths.

17. The intervertebral spinal spacer of claim 14, further comprising a third portion of the modular spacer being selectable from the plurality of spacer elements having different sizes for attachment to the modular spacer.

18. A kit for an intervertebral spacer comprising:
(a) a plurality of anterior portions for a modular spacer, each of the plurality of anterior portions for the modular spacer having a different size; and
(b) a plurality of posterior portions for a modular spacer, each of the plurality of posterior portions for the modular spacer having a different size; wherein at least one of the plurality of anterior portions is interlocked with at least one of the plurality of posterior portions, and wherein each of the plurality of anterior portions and the plurality of posterior portions define an internal cavity extending from a respective upper surface to a respective lower surface; and
further comprising: at least one fluid passage defined by at least one of the plurality of anterior portions or at least one of the plurality of posterior portions, the at least one fluid passage being in fluid communication with at least one of the internal cavities, wherein each of the internal cavities has a sidewall extending between an upper opening on the respective upper surface and a lower opening on the respective lower surface of the anterior portion or the posterior portion defining the internal cavity, and wherein the at least one fluid passage extends between an inner aperture on the sidewall and an outer aperture on the respective upper surface of the at least one of the plurality of ante nor portions or the at least one of the plurality of posterior portions.

19. The kit for an intervertebral spacer of claim 18, wherein each of the plurality of anterior portions has a different width and each of the plurality of posterior portions has a different depth.

* * * * *